United States Patent
Auer et al.

(10) Patent No.: US 6,921,833 B1
(45) Date of Patent: Jul. 26, 2005

(54) METHOD FOR THE CONTINUOUS PRODUCTION OF METHYL FORMATE

(75) Inventors: Heinz Auer, Neulussheim (DE); Jürgen Dahlhaus, Brussels (BE); Karl Fischer, Hohen-Sülzen (DE); Hans Hammer, Mannheim (DE); Jochen Kellenbenz, Bad Dürkheim (DE); Michael Schulz, Ludwigshafen (DE); Joachim Thiel, Neustadt (DE); Maximilian Vicari, Limburgerhof (DE)

(73) Assignee: BASF Aktiengesellschaft, Ludwigshafen (DE)

(*) Notice: Subject to any disclaimer, the term of this patent is extended or adjusted under 35 U.S.C. 154(b) by 122 days.

(21) Appl. No.: 10/031,166

(22) PCT Filed: Jul. 26, 2000

(86) PCT No.: PCT/EP00/07199

§ 371 (c)(1),
(2), (4) Date: Jan. 17, 2002

(87) PCT Pub. No.: WO01/07392

PCT Pub. Date: Feb. 1, 2001

(30) Foreign Application Priority Data

Jul. 26, 1999 (DE) .......................................... 199 35 038

(51) Int. Cl.$^7$ ............................................ C07C 67/36
(52) U.S. Cl. .................................................. 560/232
(58) Field of Search ................................ 560/129, 231, 560/232

(56) References Cited

U.S. PATENT DOCUMENTS

| | | | |
|---|---|---|---|
| 4,128,460 A | 12/1978 | Nishimura et al. | ........... 204/35 |
| 4,216,339 A | 8/1980 | Couteau | |
| 4,661,624 A | 4/1987 | Chang | |
| 4,734,525 A | 3/1988 | Green | |
| 4,994,603 A | 2/1991 | Mueller | |
| 5,401,873 A | 3/1995 | Zehner | |
| 5,917,085 A | 6/1999 | Lippert | |

FOREIGN PATENT DOCUMENTS

| | | |
|---|---|---|
| BR | 9100174 | 9/1992 |
| BR | 9501255-9 | 5/1997 |
| BR | 9501280-0 | 5/1997 |
| DE | 863 046 | 1/1953 |
| DE | 880 588 | 6/1953 |
| DE | 926 785 | 4/1955 |
| DE | 1 046 602 | 6/1959 |
| DE | 1 147 214 | 10/1963 |
| DE | 22 43811 | 4/1974 |
| DE | 37 10726 | 9/1977 |

(Continued)

OTHER PUBLICATIONS

Ullmann's Encyl.Ind.Chem,Fifth, Ed. vol. A12: 16–43.
CA 52:16206b.
CA 55:2486e.
CA 59:11270b.

*Primary Examiner*—Johann Richter
*Assistant Examiner*—Karl Puttlitz
(74) *Attorney, Agent, or Firm*—Novak Druce & Quigg (57) ABSTRACT

A description is given of a process for preparing methyl formate by reacting excess methanol with carbon monoxide under superatmospheric pressure and at elevated temperature in the presence of alkali metal methoxide or alkaline earth metal methoxide as catalyst in a pressure-rated reactor, in which the use of at least two reactor elements, preferably operated in countercurrent, at about 100° C. and a pressure of about 100 bar in combination with a solids-free desalting of the reaction product makes possible very economical, largely trouble-free production of methyl formate in any desired quality and with a very good production capacity.

Furthermore, the process for solids-free desalting and apparatuses for carrying out this process are described.

4 Claims, 1 Drawing Sheet

FOREIGN PATENT DOCUMENTS

| | | |
|---|---|---|
| DE | 43 09731 | 9/1994 |
| DE | 195 06555 | 8/1996 |
| EP | 048 891 | 4/1982 |
| EP | 104 875 | 4/1984 |
| EP | 251 112 | 1/1988 |
| EP | 596 483 | 5/1994 |
| GB | 1426423 | 2/1976 |
| GB | 1 432 648 | 4/1976 |
| JP | 57-126993 | 8/1982 |

METHOD FOR THE CONTINUOUS PRODUCTION OF METHYL FORMATE

BACKGROUND OF THE INVENTION

The present invention relates to a process for preparing methyl formate, to an apparatus for carrying out this process and to methyl formate which has been prepared by this process and is to be used, in particular, for preparing formic acid.

Methyl formate is used in industry predominantly for the preparation of formic acid and for this purpose is at present produced on a large scale by reaction of methanol with carbon monoxide in the presence of alkali metal alkoxide. However, the industrial implementation of this process suffers from problems which make the process inconvenient, unreliable and energy-consuming and thus considerably increase its costs.

To seek to perfect the process for industrial-scale use, the technology for carrying out the process has developed in essentially two directions: one group of processes employs a very high CO pressure with the aim of obtaining very high concentrations of methyl formate in the output from the reactor, while another group of processes makes use of a relatively low CO pressure with the aim of obtaining a relatively low concentration of methyl formate in the reaction mixture so as to avoid formation of salt deposits in the reactors, on cooling surfaces and in valves to make trouble-free operation possible over a relatively long time. DE-C-926 785 discloses a high-pressure process in which the reaction mixture is circulated and flows alternately through a reactor and a cooler. Fresh methanol and sodium methoxide dissolved therein as catalyst are fed to the top of the reactor, and the carbon monoxide or the gas mixture comprising carbon monoxide is injected under a pressure of 300 bar at the bottom of the reactor operating at from 80 to 130° C. Part of the circulating reaction mixture is continuously discharged via a pressure chamber. The process is carried out using a low catalyst concentration of not more than 0.25% by weight of sodium (corresponding to 0.59% by weight of sodium methoxide) in order to keep salt deposits as small as possible and the reactor is stirred to keep the precipitated salts in suspension.

A high outlay in terms of apparatus is required for carrying out this known process; in particular, stirring under the high pressure results in virtually insoluble engineering problems. Despite the high engineering outlay, it is not possible to prevent the difficulties associated with the formation of solid deposits in this process either. Trouble-free continuous operation of the process for acceptable periods of time is therefore not possible. For this reason, the production capacity achievable in practice is unsatisfactory and the process as a whole is uneconomical.

DE-C-1046602 discloses a continuous, two-stage process for preparing methyl formate, in the first stage of which methanol is reacted in a jacket-cooled tube reactor to a conversion of from 70 to 75% with CO, which is fed into the tube reactor in substreams at a plurality of points, at from 60 to 140° C. and a pressure of from 50 to 300 bar in turbulent flow in the presence of from 0.5 to 5% by weight of alkali metal alkanolate. The reaction mixture obtained in the first stage is then reacted with an excess of CO in an autoclave until a conversion to methyl formate of about 90%, based on methanol used, has been achieved. in this process, it is difficult to ensure the conditions required in the reactor, namely maintenance of a particular reaction temperature with simultaneous turbulent flow. In addition, industrial implementation of the process requires very difficult, very exact control of the cooling water temperature, the CO pressure and the flow velocity of the reactants. In the second stage of the process, cooling is supposed to be achieved only by introduction of precooled carbon monoxide and/or by subcooling the reaction mixture coming from the first stage. Both measures require a high outlay in terms of apparatus if malfunctions caused by encrustation are to be prevented. Furthermore, it is necessary to use a particularly pure, if necessary prepurified CO in order to avoid precipitate formation and fouling of the cooling surfaces. Although a production capacity of 1674 kg/m$^3$/h has been derived purely mathematically in the working example, this process, too, could not be introduced for continuous production of methyl formate because of the high engineering outlay, the tremendous difficulties in setting and monitoring the process conditions and the remaining intrinsic risk of blockages.

The applicants for this patent have made intensive efforts to overcome difficulties occurring in this process. These efforts have led to the process described in DE-C-1 147 214. Here, at least two substreams of carbon monoxide are fed at different levels into a tower-like reactor, so as to form different reaction zones in the reactor. In the first zone, about 75–85% of the methanol fed in, which contains from 0.12 to 0.3 mol % of alkali metal methoxide, is converted into methyl formate under a CO pressure of from 150 to 200 bar at from 30 to 100° C., and in the lower zones of the reactor the reaction is continued at from 40 to 60° C. to a conversion of about 95%. The salt-like precipitates which are naturally formed in this process are supposed to be prevented from depositing on the plant components by a sudden change in the flow of the various CO substreams carried out at regular or irregular time intervals, with the total flow being kept constant, by ensuring sufficient flow velocities of the reaction mixture and by repeated sudden opening and closing of valves through which flow occurs. However, according to the working example, this process gives a production capacity of only about 440 kg/m$^3$/h in a limited-term individual experiment.

This process variant, too, requires a high outlay for monitoring and for the sudden changes in the CO streams and the valve control to be adapted to the operating values. Despite this, deposits of catalyst and its decomposition products on plant components cannot be avoided over a prolonged operating time, which results in downtimes and a further reduction in the product capacity.

In a further high-pressure process described in DE-A-195 06 555, methanol is reacted at from 50 to 150° C. with CO under a pressure of from 210 to 250 bar in the presence of a relatively low catalyst concentration of from 0.05 to 0.2% by weight of alkali metal methoxide in a reactor or a reactor cascade. Rapid reaction is supposed to be achieved by particularly good dispersion of the carbon monoxide introduced in the reaction mixture, which is supposed to be achieved by blowing it in by means of a jet nozzle. The CO stream can be fed in as substreams and any reactor cascade used can have a temperature profile. The reaction mixture discharged from the reactor contains about 97% by weight of methyl formate and, according to the examples, the production capacity is from 530 to 960 kg/m$^3$/h.

Unreacted methanol is re-used after distillation of the reaction mixture. However, recirculation of the catalyst is not provided for, so that relatively large amounts of solid waste are formed after work-up of the crude product despite the low catalyst concentration. Furthermore, exploitation of the high conversion which is possible in principle involves an appreciable risk of deposition of encrustations in the plant, so that here, too, one has to expect plant downtimes which will drastically reduce the intrinsically good production capacities determined in individual experiments. In addition, the capital costs of the plant are high because of the high process pressures, so that the economics of the process are not fully satisfactory.

The abovementioned high-pressure processes make it possible to achieve a high methanol and CO conversion, but lead to the engineering difficulties and economic disadvantages described, especially high capital costs and salt deposits in the plant components.

A process-engineering alternative to the high-pressure processes is provided by the low-pressure processes which operate at lower CO pressures of from about 10 to 100 bar. These reaction conditions lead to a lower methanol conversion, but generally avoid precipitation of salts. Low-pressure processes are also known in various embodiments.

German patent No. 863 046 discloses a process for the continuous preparation of methyl formate, an improved embodiment of which has been described in German patent No. 880 588. In this process, a solution of sodium alkanolate containing from 1 to 2.5% by weight of sodium (corresponding to from 2.3 to 5.9% by weight of sodium methoxide when using methanol) is reacted with carbon monoxide at from 85 to 90° C. under a pressure of from 10 to 30 bar. In the process of German patent No. 863 046, the alkanolic sodium alkanolate solution and the carbon monoxide are passed once in countercurrent through the reactor, while in the improved process of DE-C-880 588 the reactants are circulated in cocurrent through the reactor. The reaction conditions temperature, flow velocity of the liquid phase and pressure are set so that at least that amount of alkanol required to keep the alkali metal alkanolates used as catalyst in solution remains unconverted. In the improved process, the methyl formate formed during passage through the reactor and excess methanol are discharged from the reactor together with the CO stream in amounts corresponding to their equilibrium vapor pressures. The flow of the CO stream should be set so that the methyl formate is removed as completely as possible from the system. The CO stream leaving the reactor is cooled to condense the entrained compounds methanol and methyl formate and the liquid mixture is discharged from the circuit. The cold carbon monoxide is then once more preheated to the reaction temperature and recirculated to the reactor.

The methanol/methyl formate mixture obtained in this way contains from 38 to 40% by weight of methanol. It is fractionally distilled and the methanol is likewise returned to the circuit. In the improved embodiment of the process as described in DE-C-880 588, a yield of only 3.1 kg of methyl formate is obtained per hour from a reactor having a volume of 770 l, according to the data in the working example. This corresponds to a production capacity of only 4.0 kg/m$^3$/h. A process having a production capacity as low as this is completely out of the question for production on an industrial scale. In addition, the unusually high catalyst concentration is accompanied by considerable disadvantages: during the reaction, there is generally a progressive reduction in the catalyst activity because of the unavoidable formation of alkali metal formate. For this reason, part of the circulating, catalyst-containing methanol always has to be discharged and a corresponding amount of fresh catalyst solution has to be added. The energy consumption required in this process for cooling and reheating the circulating carbon monoxide and for distilling the dilute methyl formate is also not inconsiderable.

German patent 22 43 811 discloses a process for the continuous preparation of methyl formate in which methanol is reacted in countercurrent with gases comprising carbon monoxide at from 50 to 130° C. in the presence of from 0.4 to 1.5% by weight of alkali metal methoxide in a column having flooded, preferably individually cooled trays.

The CO partial pressure should be in the range from 40 to 150 bar and the residence time of the reactants in the column should be from 50 to 1500 seconds. The reaction mixture obtained at the bottom after passing through the column contains from 20 to 70% by weight of methyl formate. It is worked up by distillation.

Apart from the high capital costs of the complicated column construction, a major disadvantage is that only a fraction of the components methanol and carbon mon-oxide fed in is consumed in the process and the high proportion of catalyst is poorly utilized. This leads to additional high costs which are increased further by the energy consumption for preheating the CO and for distillation of all the reaction mixture taken from the bottom of the column. Finally, there are technical problems in disposing of the catalyst- and salt-containing residues from the distillation.

U.S. Pat. No. 4,661,624 describes a process for preparing methyl formate, in which methanol is reacted with CO at from 70 to 130° C. under a pressure of from 5 to 70 bar in the presence of from 1 to 8 mol % (based on the alcohol used, corresponding to from 1.7 to 13.5% by weight of sodium methoxide) of a sodium alkoxide catalyst. The process is controlled so that the conversion is restricted to from 2 to 10% of the alcohol used, as a result of which salt deposits in the reactors are completely avoided but the content of methyl formate in the reaction product is only 1–19% by weight. The reaction mixture discharged is worked up by distillation, which requires an unjustifiably high amount of energy because of the low methyl formate content, even when utilizing the heat of reaction in an integrated heat system. The methanol obtained after the distillation together with the catalyst dissolved therein is returned to the process. However, due to the high concentration of active catalyst required, it is necessary to continually add relatively large amounts of fresh catalyst to the process. In addition, the utilization of the gas comprising carbon monoxide fed in is not satisfactory.

DE-A-43 09 731 relates to a process for preparing methyl formate, in which methanol is partially reacted in a mixing zone with carbon monoxide or gases comprising carbon monoxide at from 60 to 100° C. under a pressure of from 10 to 300 bar (in the working example, 57 bar) in the presence of from 0.4 to 1.5% by weight of alkali metal methoxide. The mixture obtained there is saturated with CO and passed to an after-reaction zone where the reaction is completed without introduction of further starting materials. In this process, too, only a low concentration of methyl formate in the reaction product is obtained, so that the energy balance for the process is unfavorable.

DE-C-27 10 726 discloses a process for preparing methyl formate in which a solution of from 0.2 to 2.5% by weight of an alkali metal methoxide or alkaline earth metal methoxide in methanol is circulated through a reactor in which the liquid phase is present in a lower section and whose upper part contains a gas phase containing from 20 to 100% by volume of carbon monoxide. The reaction is carried out at from 70 to 110° C. and a pressure of from 20 to 110 bar. The methanolic catalyst solution is fed to the reactor using an apparatus (e.g. an impingement plate) which atomizes the liquid jet injected at high velocity in the gas phase, or which draws in gas from the gas phase and injects it as fine bubbles into the liquid phase (e.g. a Venturi tube).

The liquid circuit contains a heat exchanger which allows precise setting of the temperature in the circulating liquid and a powerful pump which maintains the turbulent liquid flow. In operation, fresh methanolic methoxide solution is continuously fed to the reactor and a corresponding amount of the reaction mixture is discharged and has to be worked up by distillation.

According to this document, it is advantageous for thermodynamic reasons to set the feed of starting materials and the discharge in such a way that the reaction mixture contains from about 44 to 65% by weight of methyl formate. If the formation of precipitates is accepted, a reactor output having a methyl formate content of 82% by weight can be obtained. Although such precipitates are supposed to be tolerable according to the document, this is based on only one individual experiment carried out over a limited time. In any case, such precipitates lead to increased abrasion of the high-throughput circulation pump and any impingement elements or Venturi tube used. Isolation of methyl formate from a mixture containing only from 44 to 65% by weight of this substance leads to high energy costs. High operating costs of the process also result from the high catalyst consumption caused by the high catalyst concentration (in 5 of 6 examples, 2.5% by weight) and from the expense of properly disposing of the distillation residue. A further disadvantage of the process is that an increase in the methyl formate content of the reaction product causes a reduction in the production capacity.

Various attempts have also been made to overcome the disadvantages and difficulties associated with the above-described known processes by means of routes other than those followed hitherto.

Thus, prevention of precipitate formation and/or improvements in the production capacity by addition of complexing agents, in particular cyclic polyethers (EP-B-0 048 891), of surface-active solubilizers such as alkali metal perfluoroalkanesulfonates (EP-B0 596 483) or of inert, polar, aprotic solvents (EP-A-0 251 112) have been described. Other attempts comprise the addition of other catalysts such as amidine derivatives (EP-A-0 104 875) or of combinations of amines with ethylene oxide. These processes all have the disadvantage that they introduce additional organic materials into the reaction mixtures and these materials have to be disposed of after the work-up, which eliminates the benefits resulting from any yield improvements achieved. In addition, the purchase price of the proposed additives presents an insuperable obstacle to their industrial use.

BRIEF SUMMARY OF THE INVENTION

It has now surprisingly been found that methyl formate can be prepared in a trouble-free manner, in good yields and extremely inexpensively without complicated additives if the process described below is employed.

The present invention provides a process for preparing methyl formate by reacting excess methanol with carbon monoxide under superatmospheric pressure and at elevated temperature in the presence of alkali metal methoxide or alkaline earth metal methoxide as catalyst in a pressure-rated reactor, separating the methyl formate formed from the reaction product and recirculating the liquid phase which is essentially free of methyl formate to the reactor, with part of the liquid phase to be recirculated being discharged and fresh catalyst solution being fed in, wherein the reaction is carried out in a cascade comprising at least two reactor elements at from 80 to 120° C., under a carbon monoxide pressure of from 90 to 180 bar, in the presence of from 0.05 to 0.5% by weight, based on the weight of the liquid feed, of an alkali metal alkoxide or alkaline earth metal alkoxide, the ratio of the amounts of staring materials fed in per unit time, the reaction temperature, the pressure and the residence time of the reactants in the reactor elements are set so that at least that amount of methanol required to keep both the catalyst used and its degradation products virtually completely dissolved under the reaction conditions in the reactor and in the fresh reaction product remains unreacted, the total output from the reactor is passed to a stripping apparatus in which essentially the methyl formate is stripped from the reaction mixture, a part TR of the remaining liquid phase is recirculated to the reactor and a part TA is discharged, with the TR:TA split controlled as a function of the alkali metal formate or alkaline earth metal formate content of the degassed reaction product so that solid precipitates of alkali metal salts or alkaline earth metal salts occur at no point in the process, and residual catalyst and catalyst degradation products are removed solids-free from the discharged part in a desalting apparatus and the remaining methanol is returned directly or indirectly to the reactor.

DETAILED DESCRIPTION OF THE INVENTION

The process of the present invention is advantageously carried out using from 2 to 5, preferably from 2 to 4, cascaded reactor elements. The liquid phase of the reaction mixture, consisting essentially of methanol, methyl formate and dissolved active and consumed catalyst, can be passed through the reactor cascade in cocurrent or countercurrent to the gaseous phase consisting essentially of CO or the CO-containing gas mixture. Preference is given to countercurrent operation.

The process of the present invention is preferably carried out at from 90 to 110° C. The preferred pressure range extends from 110 to 160 bar, in particular from 110 to 140 bar. It is self-evident that the process could also be carried out at higher pressures, but this would result in one of the advantages of the process of the present invention being lost.

The catalyst used in the process of the present invention is an alkali metal alkoxide or alkaline earth metal alkoxide, preferably a methoxide. Preference is given to alkali metal methoxides, in particular sodium methoxide and potassium methoxide, which can also be used in admixture with one another. Under particular process conditions, e.g. if higher than usual methyl formate concentrations occur in individual process stages, the use of potassium methoxide can bring advantages. Purely economic aspects, e.g. the cost and/or availability of catalyst substances, may also influence the decision in favor of one of the possible catalysts or in favor of the use of a combination of these.

The catalyst used for the reaction is converted into catalytically inactive substances by unavoidable secondary reactions. Thus, traces of water form alkali metal hydroxide or alkaline earth metal hydroxide, traces of $CO_2$ lead to the formation of carbonates, reaction of the alkoxide with the methyl formate produced leads to alkali metal formate or alkaline earth metal formate and the direct reaction of alkali metal hydroxides and alkaline earth metal hydroxides with carbon monoxide also forms alkali metal formates or alkaline earth metal formates as by-product.

All the catalytically inactive products formed from the catalyst by secondary reactions will hereinafter be referred to all together as "consumed catalyst" or as "catalyst degradation products".

The preferred catalyst concentration is from 0.1 to 0.3% by weight, for example 0.2% by weight, based on the weight of the liquid feed.

It has surprisingly been found that consumption of the catalyst by secondary reactions can be significantly reduced by the cascading of the reactor elements. This could be attributable to the fact that the cascading of the reactor elements largely suppresses backmixing of the reaction mixtures present in the individual reactor elements, which has the further advantageous consequence (which has apparently not been given any attention in conventional processes) that in the process of the present invention, in contrast to many conventional processes, a comparatively low methyl formate concentration prevails in the region where the catalyst is fed in.

This gives the advantage that high, economically valuable conversions can be achieved despite low catalyst concentrations and that only relatively small amounts of consumed catalyst have to be removed from the process.

Under the above-described reaction conditions, about 30% of the catalyst is consumed during a single pass of the reactants through the reactor and the downstream work-up elements. When assessing this percentage, it has to be noted that the absolute value of catalyst consumption is decisive for the economics of the process. Owing to the low catalyst concentration required in the synthesis according to the present invention, this absolute value is considerably lower than in known processes. Naturally, an amount of methanolic solution of fresh catalyst corresponding to the amount of unconsumed and consumed catalyst discharged via the desalting stage has to be fed into the reactor.

The make-up catalyst is fed in in the form of a 10–50% strength by weight (in this range as concentrated as possible), preferably from 20 to 40% strength by weight, for example 30% strength by weight, methanolic solution.

The feed of the reactants to the synthesis reactor is advantageously regulated so that the molar ratio of methanol to carbon monoxide is from 3:1 to 0.5:1, preferably from 2:1 to 1:1.

Furthermore, the flexibility of the process is increased if the gas is introduced either at the first reactor element or at the two first reactor elements of the reactor chain, with the amounts of gas fed to the individual elements being able to be varied as required in order to establish particular desired reaction conditions therein.

The numbering of the reactor elements begins at that end of the reactor chain at which the carbon monoxide (FIGURE, No. 5) is introduced and the reaction product (FIGURE, No. 6) is taken off.

When carrying out the process of the present invention, it has been found to be particularly advantageous to set the reaction conditions in the reactor elements so that from 75 to 95%, preferably from 80 to 95%, of the heat of reaction is generated in the first of two subsections of the reaction path, and from 5 to 25%, preferably from 5 to 15%, of the heat of reaction is generated in the second subsection. Here, the subsections, particularly the first subsection, can be made up of a plurality of reactor elements. The reaction is preferably carried out in three reactor elements and controlled so that from 35 to 50% of the heat of reaction is generated in each of the first and second elements and from 5 to 15% of the heat of reaction is generated in the third element. For example, 50%, 40% and 10% or 46%, 46% and 8% of the heat of reaction can be liberated in the first, second and third reactor elements, respectively.

It is also possible to operate the reactor cascade so that the last reactor element in the chain is cooled only by the feed.

It is particularly advantageous in terms of the economics of the process of the present invention to choose reaction conditions such that the reaction product comprises from 5 to 40% by weight, preferably from 10 to 25% by weight, of methanol and from 60 to 95% by weight, preferably from 75 to 90/o by weight, of methyl formate together with consumed and unconsumed catalyst.

Furthermore, it is extremely advantageous to match the introduction of reactants and the reaction conditions in such a way that from 90 to 99%, preferably from 95 to 99%, of the carbon monoxide introduced is converted into methyl formate.

Carbon monoxide, methanol and catalyst are mixed in the reaction zone, and good dispersion of the gas makes a rapid reaction possible. For example, it is advantageous to introduce the gas into the reactor through a jet nozzle or to disperse it in the reactor by means of a suitable stirrer, e.g. a high-speed stirrer. Mixing by means of an external circuit for each reactor element is also advantageous. The carbon monoxide stream can be introduced at one point or into one reactor element, or as a plurality of substreams at various points of the reactor or into various reactor elements.

The synthesis of the methyl formate is followed in the process of the present invention by the solids-free work-up of the reaction mixture present in the reactor cascade. In principle, the work-up can be carried out under the pressure employed in the synthesis. However, it is much more advantageous, particularly with a view to the temperatures required for the work-up by distillation, to depressurize the reaction mixture to a pressure of from 5 to 25 bar, preferably from 10 to 20 bar, upstream of the stripping apparatus. To keep the circulating streams as small as possible and to avoid condensation in the compressor, the relatively small amount of released gas obtained is cooled, preferably to about room temperature or ambient temperature, to condense entrained methanol and methyl formate, then advantageously all recycled to a point upstream of the CO compressor and once more fed to the synthesis.

The total liquid phase of the reaction product remaining after depressurization, which consists of, for example, a mixture comprising about 75% by weight of methyl formate, just under 25% by weight of methanol and residual catalyst (decomposed and undecomposed) together with traces of dimethyl ether, carbon monoxide and further inerts, is subsequently treated in a distillation apparatus to vaporize the major part of the methyl formate. Naturally, a certain proportion of the methanol present in the reaction product is vaporized at the same time. For the vaporization of the methyl formate, the pressure over the reaction product is advantageously reduced further so that a pressure of from 1.2 to 2.5 bar, preferably from 1.5 to 2.0 bar, is established at the top of the distillation apparatus. At least part of the heat of vaporization required for the vaporization is generally present in the hot reaction product. The remainder is covered by direct heating of the distillation apparatus or by supply of heat transfer media.

Depending on the desired purity of the methyl formate prepared, the reflux ratio in the distillation apparatus is set so that from 85 to 90% purity by weight methyl formate can be taken off at the top.

The part of the reaction mixture remaining after the methyl formate has been separated off consists essentially of methanol containing active and consumed catalyst. This solution is divided into a part TR which is recirculated straight back to the reactor cascade and a part TA which is discharged from the circuit. As mentioned above, the TR:TA split is controlled as a function of the alkali metal formate or alkaline earth metal formate content of the degassed reaction product, with the objective being to set the split so that solid precipitates of alkali metal salts or alkaline earth metal salts occur at no point in the process. This is achieved by setting TR and TA so that the amount of deactivated catalyst leaving the process via the desalting apparatus corresponds to the amount which is consumed in a single pass through the reactor and in the further process stages. Of course, some still-active catalyst goes to the desalting apparatus, so that this proportion leaves the process.

It is advantageous to control the split so that the alkali metal formate or alkaline earth metal formate content at the reactor outlet is from 0.05 to 0.5% by weight, preferably from 0. 1 to 0.3% by weight.

On the basis of experience, from 20 to 80% of the catalyst-containing methanol remaining after the methyl formate has been separated off is discharged to maintain constant operation of the synthesis.

The discharged part TA of the methanol containing catalyst and catalyst degradation products is subsequently desalted in a solids-free manner. For this purpose, sufficient steam and/or hot water and possibly additional heat are introduced into this liquid phase in the desalting apparatus for the methanol to be essentially completely vaporized and for an aqueous solution of the catalyst degradation products to be obtained. The expression "catalyst degradation product" here includes the alkali metal hydroxide or alkaline earth metal hydroxide formed from residual active catalyst and water.

In this operation, the amount of steam and/or hot water is set so that the catalyst and its degradation products are reliably maintained in aqueous solution. In general, this condition is met when the concentration of catalyst degradation products in the aqueous output from the desalting apparatus is from 5 to 20% by weight, preferably from 6 to 12% by weight, for example 8% by weight.

Preferably, steam at a pressure of from 2 to 6 bar, preferably from 3 to 5 bar, e.g. in the form of direct steam, is fed to the desalting apparatus.

It is of particular economic interest to operate the desalting apparatus as part of an integrated heat system with the distillation apparatus, with the methanol vapor leaving the top of the desalting apparatus being fed to the distillation apparatus.

In this case, particular advantages are obtained when the pressure at the top of the desalting apparatus is selected so that the vapor stream from the top of this apparatus can be fed directly to the distillation apparatus.

The process used here for desalting methanol containing residual active catalyst and consumed catalyst in a solids free manner is likewise a subject matter of the present invention. The particular value of this part of the process is that it makes it possible to carry out the entire methyl formate synthesis without solids being present.

Apart from the catalyst, the methanol consumed in the synthesis has to be fed to the reactor cascade. The methanol used in the process of the present invention is chemical-grade or technical-grade methanol. It can also be recycled from other processes, e.g. the hydrolysis of methyl formate to formic acid and methanol. In order to ensure a very low catalyst consumption, preference is given to using methanol whose water content is less than 100 ppm, preferably less than 30 ppm, in particular in the range from 5 to 15 ppm.

For the same reason and to achieve a very high conversion of the reactants, it is advantageous to use carbon monoxide in the form of a gas mixture comprising carbon monoxide and having a CO content of from 45 to 100% by volume, preferably from 70 to 100% by volume, in particular from 90 to 100% by volume. When using such gas mixtures, the total pressure is preferably set so that the carbon monoxide partial pressure is in the range from 90 to 180 bar.

The CO-containing gas phase may comprise gases which are inert under the conditions of the synthesis, e.g. hydrogen, nitrogen, hydrocarbons.

Under certain conditions, e.g. if the process of the present invention is operated as part of an integrated system with other processes or particularly favorable procurement conditions apply, it can also be economically advantageous to operate the process of the present invention using waste gas containing about 50% by volume of CO. Owing to the ability of the process to be adapted to changes in the process conditions, a good yield of methyl formate in any desired purity can also be achieved when using such a waste gas. Yields of methyl formate of over 90 mol % and even over 95 mol %, based on CO used, are usually achieved by the process of the present invention. Based on methanol used, the yields are virtually 100 mol % when using a CO-containing gas mixture containing a high percentage of CO or pure CO. A further advantage of the process of the present invention is that the wastewater discharged from the desalting apparatus contains only from 15 to 30 ppm, generally about 20 ppm, of methanol, i.e. virtually no methanol.

The cooler employed in the process is operated using river water and/or cold water.

The process of the present invention makes it possible to achieve, at low catalyst concentrations and intermediate pressures, a high space-time yield of from 400 to over 1000 kg/m$^3$/h at final methyl formate concentrations of over 80% by weight. The low catalyst concentration necessary helps to achieve a significant reduction in starting material costs, while the moderate synthesis pressure avoids the high capital costs for high-pressure plants. Furthermore, the process of the present invention allows the plant to be controlled so that no salt precipitates occur, as a result of which blockage problems are eliminated and the availability of the plant and thus the annual capacity is considerably increased. The methanol conversion is significantly higher than in the case of the typical low-pressure processes and the amount of methanol to be circulated is therefore also considerably smaller. The work-up of the present invention requires very little energy and nevertheless leads to a methyl formate whose concentration is so high that it can be used directly for further reactions, e.g. hydrolysis to formic acid.

A further advantageous feature of the process of the present invention is its great ability to be adapted to changes in the reaction conditions which one wishes to make in order to set a particular desired quality of the end product. Furthermore, the process can also be carried out without disadvantages in one and the same apparatus using different catalysts, different amounts of catalyst and different CO qualities depending on availability. A particular engineering advantage is the fact that the parameters of the process of the present invention can be varied within wide limits without resulting in precipitation of catalyst and catalyst degradation products, e.g. alkali metal formates or alkaline earth metal formates. For this reason, no solid deposits are formed on the inner surfaces of the plant, in particular on the heat exchange surfaces, so that problems with controlling the temperature in the individual plant sections and with pipe blockages, as regularly occur in the case of known high-pressure processes, are completely avoided.

The conversion in the reaction can be controlled both via the position of the thermodynamic equilibrium, which can be influenced by adjustment of pressure and temperature, and via the stoichiometry and/or residence time of the reactants in the reactor. High final conversions reduce the amounts of unconsumed starting materials which are obtained in the work-up and have to be recirculated to the reaction. CO conversions of from 90 to 99% of theory have been found to be useful.

A further advantage of the process of the present invention is that, due to the high CO conversion in contrast to many known processes, either no recirculation of unreacted CO is necessary at all, which eliminates capital costs for compressors, or, if recirculation of the small amount of unreacted carbon monoxide is desired, this can be brought about using a minimum of compression work.

The process of the present invention with its working pressure of from 90 to 160 bar, which is considerably above that of present-day low-pressure processes, is an intermediate-pressure to high-pressure process according to current nomenclature. In known processes operating at above 100 bar, no catalyst is recirculated. The entire catalyst used is lost after a single pass through the reactor. A further complication occurring in known high-pressure and intermediate-pressure processes is the formation of methyl formate/methanol/salt suspensions from which the salts can be separated only by means of complicated solids handling.

In the case of known low-pressure and intermediate-pressure processes in which catalyst recirculation is necessary, the introduction of water into the circuit is strictly avoided because the catalyst is destroyed by water. Since consumed catalyst has to be removed from the system in these processes too, it likewise has to be discharged in these cases by methods of solids handling technology, e.g. by filtration or centrifugation.

It has now surprisingly been found that in the process of the present invention part of the unconsumed catalyst can be recycled without encrustations occurring in apparatus components, in particular on the heat exchangers. In addition, the process of the present invention completely avoids the technically complicated handling of solids since it has surprisingly been found to be possible to carry out this separation by purely thermal distillation means in a solids-free manner and to configure the process so that consumed catalyst is discharged as an aqueous solution and, despite the introduction of water, a substantial proportion of the unconsumed catalyst can be recirculated to the synthesis.

The present invention further provides a plant for producing methyl formate by the above-described process of the present invention, comprising A) a synthesis group consisting essentially of
  A1) a reactor having at least two separately heatable and coolable reactor elements with feed lines for fresh methanol, recirculated catalyst-containing methanol for fresh methanolic catalyst solution and for a gas mixture comprising carbon monoxide, at least one outlet line each for the reaction product and residual gas, devices for generating and maintaining a fine dispersion of the gas stream in the liquid stream, and instrumentation for monitoring temperature and pressure,
  A2) a depressurization apparatus provided with cooling elements for depressurizing the reaction product to the work-up pressure and provided with a feed line for the reaction product and outlet lines for residual gas and liquid phase, B) a work-up group consisting essentially of
  B1) a distillation apparatus for separating essentially methyl formate from the liquid phase of the reaction product provided with a feed line for the liquid phase and outlet lines for essentially methyl formate and for remaining catalyst-containing methanol,
  B2) an adjustable stream divider for dividing the methanol stream containing residual catalyst and catalyst degradation products leaving the distillation apparatus into the substreams TR and TA,
  B3) a desalting apparatus which may be provided with heating and cooling elements and operates in a solids-free manner, provided with inlets for methanol containing residual catalyst and catalyst degradation products and for hot water or steam and outlets for methanol vapor and for aqueous salt solution, C) connection lines and, if required, pumps for appropriate transport of reaction participants and products between the elements of the plant sections A and B and feed lines for starting materials and outlet lines for methyl formate and waste gas.

The FIGURE shows, schematically and by way of example, the plant of the present invention for preparing methyl formate and the desalting apparatus of the present invention integrated therein. In a preferred embodiment, the desalting apparatus forms a directly integrated heat system with the distillation apparatus.

BRIEF DESCRIPTION OF THE DRAWING

Section A of the FIGURE shows the synthesis group comprising a reactor (1) with three reactor elements and feed lines for fresh methanol (2), recirculated catalyst-containing methanol (3), for fresh methanolic catalyst solution (4) and for a gas mixture (5) comprising carbon monoxide, an outlet line each for the reaction product (6) and residual gas (7), devices for generating and maintaining a fine dispersion of the gas stream in the liquid stream (8) and a depressurization apparatus (10) provided with cooling elements (9) for depressurizing the reaction product to the work-up pressure, with a feed line (11) for the reaction product and outlet lines for residual gas (12) and liquid phase (13).

Section B of the FIGURE shows the work-up group comprising a distillation apparatus (14) for separating essentially methyl formate from the liquid phase of the reaction product, with a feed line (15) for the liquid phase and outlet lines for essentially methyl formate (16) and for remaining catalyst-containing methanol (17), an adjustable stream divider (18) for dividing the methanol stream containing residual catalyst and catalyst degradation products leaving the distillation apparatus into the substreams TR and TA, the solids-free desalting apparatus (19) with inlets for methanol (20) containing residual catalyst and catalyst degradation products and hot water or steam (21) and outlets for methanol vapor (22) and aqueous salt solution (23), a cooling apparatus (24) for the methyl formate coming from line (16) of the distillation apparatus (14) and outlets for the cooled methyl formate (25) and for residual gas (26). The FIGURE also shows the pumps (27a and 27b) as auxiliary equipment.

Figure 1:
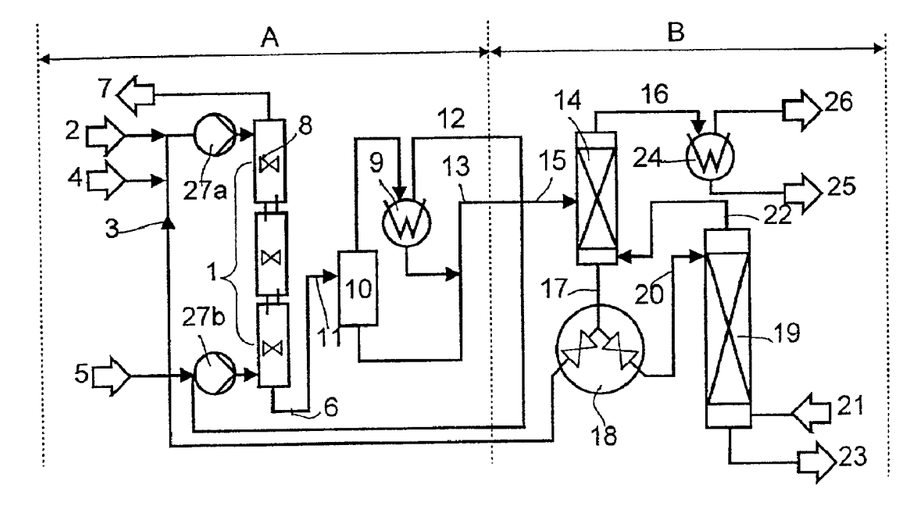

The reactor elements can be constructed as vessels or tube reactors. It is not necessary for each reactor element to be configured as a single equipment item. Rather, it is possible to use any reactor construction which performs the function of a plurality of reactor elements connected in series. It is therefore readily possible to use an individual reactor which is divided into at least two, preferably from 2 to 5, in particular from 2 to 4, reaction zones by means of suitable internals. When reactor elements are referred to in the following, this term is intended also to include the reaction zones into which an individual reactor is divided. Conversely, the term "reaction zone" also encompasses single reactor elements. Such a reactor, too, can be constructed as a vessel or tube reactor.

The reactor elements advantageously have their own, regulatable feed and outlet lines for reactants and products and, if appropriate, their own heatable or coolable external circuits. Furthermore, temperature and pressure of the reactor elements can be controlled individually. The cascade can have a temperature profile or else be operated at a uniform temperature. Reactors having internal cooling systems or jacket cooling or an external circuit with heat exchangers can be used for the process of the present invention.

These construction features which are advantageous for the plant of the present invention are expediently achieved when using a single reactor divided into zones.

It is therefore useful to configure the reactor so that it can be heated and/or cooled in zones.

Furthermore, such a single reactor advantageously has a plurality of feed lines for reactants and outlet lines for outlets distributed over its length and assigned to the individual reaction zones as well as, if appropriate, heatable and/or coolable external circuits assigned to the reaction zones.

The devices installed in the reactor or the reactor elements for finely dispersing the reactants are, for example, sieve trays, frits or jet nozzles. It is also advantageous for the reactor elements or the reactor divided into zones to have baffles and/or stirring devices.

The distillation apparatus B1 of the production plant of the present invention has the function of distilling the methyl formate from the feed stream, i.e. separating it off by selective vaporization. To prepare a methyl formate suitable for formic acid production, a simple stripping column is generally satisfactory for the distillation task. However, it is also possible to provide the column with a rectification section so as to be able to take off a methyl formate stream of high purity at the top. This column is then operated under reflux as a rectification column.

Such a column consists essentially of a tubular hollow body which is provided with separation plates, can if necessary be heated or cooled in zones and has an inlet for the degassed reaction product at a suitable position, outlets for taking off the distillate at the top and methanol containing catalyst and catalyst degradation products at the bottom, and, if appropriate, further feed lines for liquid or gaseous heat transfer media.

Use is advantageously made here of a column whose separation efficiency is sufficient to take off methyl formate of the required purity from the degassed reaction product via the top.

In general, the column is set up for recovery of 85–90% purity by weight methyl formate (remainder=methanol). The methyl formate formed is advantageously distilled off from the reaction mixture in a simple stripping column without separation plates so that a concentration increase from 70–80% by weight (the concentration in the reaction mixture) to 85–90% by weight is achieved. This requires considerably less energy than distillation to give 95–97% purity methyl formate. Methyl formate prepared according to the present invention and having a purity of, for example, from 85 to 90% by weight has many industrial uses. In particular, it can be used directly for the hydrolysis to prepare formic acid.

The desalting apparatus B3 consists essentially of a rectification column which can be heated or cooled in zones if necessary, may be provided with separation plates and is equipped in suitable positions with feed lines for methanol containing residual catalyst and catalyst degradation products and for hot water and/or steam, outlet lines for taking off distillate at the top and water containing catalyst degradation products from the bottom. This rectification column needs to have a separation efficiency which is sufficient to take off methanol containing less than 100 ppm, preferably less than 30 ppm, in particular from about 5 to 15 ppm, of water at the top. In general, a simple stripping column is satisfactory for this purpose.

The steam or hot water supplied to the desalting apparatus is introduced into the apparatus in or preferably below the region of the inlet for the methanol containing residual catalyst and catalyst degradation products, in particular in the bottom region.

The methanol taken off at the top of the desalting apparatus can be condensed and either recirculated to the synthesis group or vaporized under such a pressure that it can be fed as gaseous heat transfer medium to the distillation apparatus. This would then require a further vaporizer at the bottom of the distillation column.

However, it is particularly advantageous and economical to operate the distillation apparatus and the desalting apparatus as a directly integrated heat system by setting the pressure at the top of the desalting apparatus to a value which is sufficiently high for the methanol vapor discharged therefrom to be introduced directly into the distillation apparatus as gaseous heat transfer medium. It is in principle also possible to combine, by means of an equivalent integrated construction, the distillation column and the desalting column into one column which is provided with side outlets and inlets for liquid phases.

A further, particularly economical embodiment of the present invention is to operate the work-up equipment, in particular the desalting apparatus, using the heat from the reactor, if appropriate with installation of a heat pump.

The present invention further provides the above-described solids-free desalting apparatus consisting essentially of a rectification column which can be heated or cooled in zones if necessary, may be provided with separation plates and has inlets for methanol containing residual catalyst and catalyst degradation products and for hot water and/or steam in suitable positions, outlets for taking off distillate at the top and water containing catalyst degradation products from the bottom, and whose separation efficiency is sufficient to take off methanol containing less than 100 ppm, preferably less than 30 ppm, in particular from about 5 to 15 ppm, of water at the top.

In a preferred embodiment, the steam or hot water supplied to the desalting apparatus is introduced into the apparatus in or preferably below the region of the inlet for the methanol containing residual catalyst and catalyst degradation products, in particular in the bottom region.

The present invention further provides the above-described combination of distillation apparatus and desalting apparatus in which the methanol vapor leaving the top of the desalting apparatus is introduced as heat transfer medium into the distillation apparatus. The following examples illustrate the process of the present invention and the apparatus of the present invention used for carrying it out.

EXAMPLE 1

Three upright tube reactors each having a volume of 2 l and each fitted with an external circuit with heat exchangers, feed lines for liquid phase and outlet lines for gas phase in the top region and outlet lines for liquid phase and jet nozzle inlets for gas phase in the bottom region were connected in series above one another so that gas phase introduced at the bottom of the lowermost reactor can flow upward through all three reactors in succession and liquid phase fed in in the top region of the uppermost reactor can flow downward through all three reactors in succession.

This synthesis arrangement was used to carry out 12 experiments in which methanol and catalyst in the form of a methanolic alkali metal methoxide solution were fed in at the top of the reactor cascade and CO was fed in from below via the jet nozzles. The feed flows are indicated in Table 1. The pressure and the temperature in the reactors were set to the values likewise shown in Table 1.

The product taken off at the bottom of the reactor cascade was depressurized in a depressurization apparatus to a pressure of 15 bar and the released gas obtained was cooled to room temperature in a two-stage cooler to condense gaseous entrained methanol and methyl formate. The remaining gas phase is recirculated to the reactor cascade, and the combined liquid phases were analyzed for methyl formate by gas chromatography and wet chemical analysis.

The last 4 columns of Table 1 show the experimental results obtained.

The abbreviations used in the table have the following meaning:

STY is the production capacity, based on the total volume of all reactors used,

NaOMe is sodium methoxide, KOMe is potassium methoxide and MeFo is methyl formate.

The conversions reported are based on methanol used.

To work up the reaction product further, it is fed to a simple stripping column in which the methyl formate is largely stripped out at a pressure of about 1.8 bar by means of methanol vapor fed into the column.

The mixture of methanol and consumed and unconsumed catalyst taken off at the bottom of this column is passed to a stream divider from which ⅓ of the mixture is recirculated to the reactor cascade and ⅔ is fed to the desalting column. In the desalting column, the catalyst- and salt-containing methanolic solution fed in is treated with 4 bar steam at an internal pressure of about 2 bar. The amount of steam fed in is set so that virtually water-free methanol vapor can be taken off at the top of the column. This methanol vapor is advantageously introduced directly as heat transfer medium into the distillation column. An aqueous alkali metal hydroxide and alkali metal formate solution is taken off at the bottom of the desalting column.

EXAMPLE 2

Two tube reactors having a length of 200 cm and an internal diameter of 4.5 cm (volume=3.15 l) and provided with an internal heat exchange tube, inlets for liquid and gas phase in the bottom region and outlets for liquid and gas phase in the top region, with the inlets for the gas phase being configured as jet nozzles, were connected in series above one another in such a way that liquid phase and gas phase introduced at the bottom of the lowermost reactor can flow upward in cocurrent through all three reactors in succession.

This synthesis arrangement was used to carry out 19 experiments in which methanol, catalyst in the form of a methanolic alkali metal methoxide solution and, through the jet nozzle, CO were fed from the bottom into the reactor cascade. The feed flows are indicated in Table 2. The pressure and the temperature in the reactors were set to the values likewise shown in Table 2.

The last 4 columns of Table 2 show the experimental results obtained.

The further work-up of the reaction product was carried out as described in Example 1.

TABLE 1

Experiments in countercurrent

| Ex. No. | CO[l/h] | MeOH [kg/h] | Catalyst Type | [% by wt.][1] | Pressure [bar] | Temperature [° C.], measured in the middle of the reactors R | | | MeFo in the output [% by wt.] | Salt precipitation [yes/no] | Conversion[2] [%] | STY [kg/m³/h] |
|---|---|---|---|---|---|---|---|---|---|---|---|---|
| | | | | | | R1 | R2 | R3 | | | | |
| 1 | 1110 | 2.5 | NaOMe | 0.20 | 109 | 90 | 90 | 90 | 75 | No | 61.5 | 520 |
| 2 | 1790 | 2.9 | NaOMe | 0.20 | 136 | 90 | 90 | 88 | 80 | No | 68.1 | 750 |
| 3 | 1120 | 2.3 | NaOMe | 0.30 | 95 | 90 | 90 | 85 | 74 | No | 60.3 | 580 |
| 4 | 1540 | 3.3 | NaOMe | 0.30 | 111 | 90 | 90 | 84 | 74 | No | 60.3 | 830 |
| 5 | 970 | 2.6 | NaOMe | 0.20 | 97 | 100 | 100 | 90 | 67 | No | 52.0 | 550 |
| 6 | 1640 | 3.5 | NaOMe | 0.20 | 117 | 100 | 100 | 90 | 73 | No | 59.1 | 880 |
| 7 | 1600 | 3.5 | NaOMe | 0.30 | 97 | 100 | 100 | 95 | 68 | No | 53.1 | 790 |
| 8 | 720 | 1.5 | KOMe | 0.20 | 112 | 90 | 90 | 76 | 73 | No | 59.1 | 370 |
| 9 | 950 | 2.0 | KOMe | 0.20 | 126 | 90 | 90 | 72 | 75 | No | 61.5 | 520 |
| 10 | 950 | 2.0 | KOMe | 0.26 | 105 | 90 | 90 | 82 | 73 | No | 59.1 | 480 |
| 11 | 970 | 2.5 | KOMe | 0.26 | 95 | 100 | 100 | 91 | 63 | No | 47.6 | 520 |
| 12 | 1590 | 3.5 | KOMe | 0.26 | 116 | 100 | 100 | 79 | 69 | No | 54.3 | 790 |

[1]based on the weight of the liquid feed
[2]based on methanol used

TABLE 2

Experiments in cocurrent

| Ex. No. | CO [l/h] | MeOH [kg/h] | Catalyst Type | Catalyst [% by wt.]¹ | Pressure [bar] | Temperature [° C.], measured in the middle of the reactors R | | MeFo in the output [% by wt.] | Salt precipitation [yes/no] | Conversion² [%] | STY [kg/m³/h] |
|---|---|---|---|---|---|---|---|---|---|---|---|
| | | | | | | R1 | R2 | | | | |
| 1 | 1864 | 2.99 | NaOMe | 0.18 | 130 | 100 | 100 | 76.9 | No | 64.0 | 560 |
| 2 | 1836 | 2.97 | NaOMe | 0.20 | 110 | 100 | 110 | 69.4 | No | 54.8 | 470 |
| 3 | 1952 | 2.91 | NaOMe | 0.21 | 120 | 100 | 110 | 73.5 | No | 59.7 | 510 |
| 4 | 2101 | 2.97 | NaOMe | 0.20 | 140 | 100 | 110 | 79.0 | No | 66.7 | 580 |
| 5 | 2186 | 3.01 | NaOMe | 0.20 | 150 | 100 | 110 | 81.0 | No | 69.5 | 610 |
| 6 | 1798 | 2.99 | NaOMe | 0.20 | 140 | 90 | 100 | 80.2 | No | 68.4 | 600 |
| 7 | 1721 | 2.59 | NaOMe | 0.25 | 140 | 90 | 100 | 86.8 | No | 77.8 | 590 |
| 8 | 1428 | 2.99 | NaOMe | 0.12 | 140 | 100 | 110 | 70.6 | No | 56.2 | 480 |
| 9 | 2031 | 4.00 | NaOMe | 0.21 | 140 | 100 | 110 | 80.2 | No | 68.4 | 790 |
| 10 | 2330 | 4.99 | NaOMe | 0.21 | 140 | 100 | 110 | 72.3 | No | 58.2 | 840 |
| 11 | 1851 | 3.11 | NaOMe | 0.30 | 140 | 100 | 110 | 80.5 | No | 68.8 | 620 |
| 12 | 2430 | 5.89 | NaOMe | 0.21 | 140 | 100 | 110 | 66.1 | No | 51.0 | 870 |
| 13 | 2064 | 4.19 | NaOMe | 0.19 | 140 | 100 | 110 | 73.8 | No | 60.0 | 720 |
| 14 | 2484 | 4.90 | NaOMe | 0.32 | 140 | 100 | 110 | 74.7 | No | 61.2 | 860 |
| 15 | 2722 | 6.01 | NaOMe | 0.31 | 150 | 100 | 110 | 71.3 | No | 57.0 | 990 |
| 16 | 1706 | 3.56 | NaOMe | 0.12 | 160 | 100 | 110 | 71.1 | No | 56.8 | 590 |
| 17 | 1857 | 3.55 | NaOMe | 0.15 | 160 | 100 | 110 | 75.8 | No | 62.6 | 650 |
| 18 | 2002 | 4.09 | NaOMe | 0.19 | 140 | 100 | 95 | 73.7 | No | 59.9 | 710 |
| 19 | 2564 | 3.77 | NaOMe | 0.21 | 140 | 95 | 110 | 78.2 | No | 65.7 | 730 |

We claim:

1. A process for preparing methyl formate by reacting excess methanol with carbon monoxide under superatmospheric pressure and at elevated temperature in the presence of alkali metal methoxide or alkaline earth metal methoxide as catalyst in a pressure-rated reactor, separating the methyl formate formed from the reaction product and recirculating the liquid phase which is essentially free of methyl formate to the reactor, with part of the liquid phase to be recirculated being discharged and fresh catalyst solution being fed in, wherein the reaction is carried out in a cascade comprising at least two reactor elements at from 80 to 120° C., under a carbon monoxide pressure of from 90 to 180 bar, in the presence of from 0.05 to 0.5% by weight, based on the weight of the liquid feed, of an alkali metal alkoxide or alkaline earth metal alkoxide, the molar ratio of carbon monoxide to methanol is set from 3:1 to 0.5:1, whereby at least that amount of methanol required to keep both the catalyst used and its degradation products virtually completely dissolved under the reaction conditions in the reactor and in the fresh reaction product remains unreacted, the total output from the reactor is passed to a distilling apparatus in which essentially the methyl formate is stripped from the reaction mixture, a part TR of from 80 to 20% of the remaining liquid phase is recirculated to the reactor and a part TA is discharged, and residual catalyst and catalyst degradation products are removed solids-free from the discharged part in a desalting apparatus and the remaining methanol is returned directly or indirectly to the reactor.

2. A process as claimed in claim 1 carried out using from 2 to 5 reactor elements.

3. A process as claimed in claim 1, wherein steam and/or hot water and, if desired, additional heat are fed to the discharged part TA of the liquid phase remaining after separating off the methyl formate, consisting essentially of methanol containing catalyst and catalyst degradation products, in the desalting apparatus in such amounts that the methanol is essentially completely vaporized and an aqueous solution of the catalyst degradation products is obtained.

4. A process as claimed in claim 1, wherein the desalting apparatus is operated as an integrated heat system with the distillation apparatus and the methanol vapor leaving the top of the desalting apparatus is fed to the distillation apparatus.

* * * * *